(12) United States Patent
Lee et al.

(10) Patent No.: US 9,874,862 B2
(45) Date of Patent: Jan. 23, 2018

(54) METHOD AND DEVICE TO MONITOR AND ANALYZE BIOSIGNAL OF USER

(71) Applicant: Samsung Electronics Co., Ltd., Suwon-si (KR)

(72) Inventors: Tak Hyung Lee, Suwon-si (KR); Yeong Sook Chae, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 318 days.

(21) Appl. No.: 14/691,074

(22) Filed: Apr. 20, 2015

(65) Prior Publication Data

US 2016/0070245 A1 Mar. 10, 2016

(30) Foreign Application Priority Data

Sep. 5, 2014 (KR) .................. 10-2014-0118823

(51) Int. Cl.
| | |
|---|---|
| *G05B 13/02* | (2006.01) |
| *G05B 19/18* | (2006.01) |
| *G05B 15/02* | (2006.01) |
| *A61B 5/00* | (2006.01) |
| *G06F 1/16* | (2006.01) |
| *G06F 3/01* | (2006.01) |

(52) U.S. Cl.
CPC ............... *G05B 15/02* (2013.01); *A61B 5/00* (2013.01); *G06F 1/163* (2013.01); *G06F 3/011* (2013.01)

(58) Field of Classification Search
CPC ........... A61B 5/04004; A61B 5/04012; A61B 5/4082; A61B 5/0402; A61B 5/0482; A61B 5/165

USPC ......................... 700/49, 59, 61, 62
See application file for complete search history.

(56) References Cited

U.S. PATENT DOCUMENTS

| | | | |
|---|---|---|---|
| 8,106,781 B2 | 1/2012 | Pietersen | |
| 2007/0022112 A1* | 1/2007 | Asukai | ............... G06F 17/30038 |
| 2008/0171573 A1* | 7/2008 | Eom | ................. H04M 1/72572 |
| | | | 455/556.2 |
| 2009/0030289 A1 | 1/2009 | Katayama et al. | |
| 2009/0122147 A1* | 5/2009 | Takashima | ............... A61B 5/16 |
| | | | 348/207.99 |
| 2013/0057660 A1* | 3/2013 | Kim | ........................ A61B 5/743 |
| | | | 348/51 |
| 2013/0150741 A1* | 6/2013 | Noh | ......................... A61B 5/18 |
| | | | 600/508 |

FOREIGN PATENT DOCUMENTS

| | | |
|---|---|---|
| JP | 2004-181218 A | 7/2004 |
| KR | 10-0425342 B1 | 3/2004 |
| KR | 10-2007-0110158 A | 11/2007 |
| KR | 10-2010-0080730 A | 7/2010 |
| KR | 10-2012-0040429 A | 4/2012 |
| KR | 10-2012-0136716 A | 12/2012 |
| KR | 10-2013-0072428 A | 7/2013 |
| KR | 10-1390845 B1 | 5/2014 |

* cited by examiner

*Primary Examiner* — Michael J Brown
(74) *Attorney, Agent, or Firm* — NSIP Law

(57) ABSTRACT

A method and device to monitor and analyze a biosignal are provided. The device may measure a biosignal from a user of the device, analyze an emotion event associated with the user of the device based on the biosignal, and generate a control command in response to a result of analyzing the emotion event. The generated control command may be used to control an external device.

19 Claims, 8 Drawing Sheets

METHOD AND DEVICE TO MONITOR AND ANALYZE BIOSIGNAL OF USER

CROSS-REFERENCE TO RELATED APPLICATION(S)

This application claims the benefit under 35 USC 119(a) of Korean Patent Application No. 10-2014-0118823, filed on Sep. 5, 2014, in the Korean Intellectual Property Office, the entire disclosure of which is incorporated herein by reference for all purposes.

BACKGROUND

1. Field

The following description relates to a device and method to monitor a biosignal.

2. Description of Related Art

A camera takes an image of an area in which individuals or wards are located. For example, the camera takes images of children in a daycare and of seniors in an assisted living facility in order to monitor the individuals providing care and the children and seniors themselves. In addition, a guardian reviews an image taken in real time since the guardian has access to the camera through wired/wireless communication, for example, the Internet.

However, since the camera allows real time monitoring of the individual and/or individuals taking care of the children or of the seniors, the individual or individuals may feel pressured which may hamper the ability of the individual to adequately take care of the children or the seniors in particular during an accident or a dangerous incident.

Therefore, since an image is continuously recorded although a special circumstance does not occur, unnecessary data may be produced and accumulated.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a device configured to monitor a biosignal of a user of the device, the device including a biosignal measurer configured to measure a biosignal from the user of the device, an analyzer configured to analyze an emotion event associated with the user of the device based on the biosignal, and a command generator configured to generate a control command in response to a result of analyzing the emotion event.

The control command generated by the command generator may control an external device to perform a predetermined operation in response to the result of analyzing the emotion event.

The control command generated by the command generator may correspond to an emotion state of the user of the device in response to the emotion state of the user of the device analyzed from the emotion event.

The device to monitor a biosignal (hereinafter, a biosignal monitoring device) may further include a communicator configured to transmit event information associated with the emotion event to an external device.

The control command generated by the command generator may control the communicator to transmit the event information in response to the emotion event being determined to be a predetermined emotion state.

The biosignal monitoring device may further include a storage configured to generate and store the event information in response to the result of analyzing the emotion event. The control command generated by the command generator may control the communicator to provide the event information to the external device in response to a connection request of the external device to the event information.

The biosignal monitoring device may further include a recorder configured to record at least one of image information and sound information associated with at least one of the user and an ambient environment of the user, and a communicator configured to transmit at least one of image information and sound information corresponding to a time interval in which the emotion event has occurred, in response to the emotion event being determined to be a predetermined emotion state.

The biosignal monitoring device may further include a motion information measurer configured to measure motion information of the user of the device. The analyzer is configured to determine the emotion event based on a change in a biosignal associated with the motion information.

The biosignal monitoring device may further include a location information measurer configured to measure location information of the user of the device. The analyzer is configured to determine the emotion event based on the location information.

The biosignal may include at least one of a bio-electrical signal, for example, an ExG signal, an electrocardiogram (ECG) signal, an electroencephalogram (EEG) signal, an electromyography (EMG) signal, and an electrooculogram (EOG) signal, a bio-optical signal, a skin temperature signal, a bio-impedance signal, and a pressure signal, for example, a signal indicating a change in a volume of the chest caused by a blood pressure and a respiration.

In another general aspect, there is provided a device configured to analyze a biosignal of a user, the device including a communicator configured to receive a biosignal measured from the user of the device, an analyzer configured to analyze an emotion event associated with the user of the device based on the biosignal, and a command generator configured to generate a control command for controlling at least one of the device and an external device in response to the emotion event.

The control command generated by the command generator may control at least one of the device and the external device to perform an operation corresponding to an emotion state of the user of the device in response to the emotion state of the user of the device analyzed from the emotion event.

In still another general aspect, there is provided a method to monitor a biosignal of an individual, the method including measuring a biosignal from the individual, analyzing an emotion event associated with the individual based on the biosignal, and generating a control command in response to a result of analyzing the emotion event.

The generated control command controls an external device to perform a predetermined operation in response to the result of analyzing the emotion event.

The generated control command corresponds to an emotion state of the individual in response to the emotion state of the individual analyzed from the emotion event.

The method of monitoring a biosignal (hereinafter, a biosignal monitoring method) may further include transmitting event information associated with the emotion event to an external device.

The transmitting of the event information may include transmitting the event information in response to the emotion event being determined to be a predetermined emotion state.

The biosignal monitoring method may further include generating and storing the event information in response to the result of analyzing the emotion event. The transmitting of the event information may include providing the event information to the external device in response to a connection request of the external device to the event information.

The biosignal monitoring method may further include recording at least one of image information and sound information associated with at least one of the individual and an ambient environment of the individual, and transmitting at least one of image information and sound information corresponding to a time interval in which the emotion event has occurred in response to the emotion event being determined to be a predetermined emotion state.

The biosignal monitoring method may further include measuring at least one of motion information and location information of the individual. The analyzing of the emotion event may include determining the emotion event based on a change in a biosignal associated with at least one of the motion information and the location information.

Other features and aspects will be apparent from the following detailed description, the drawings, and the claims.

Figure 1:
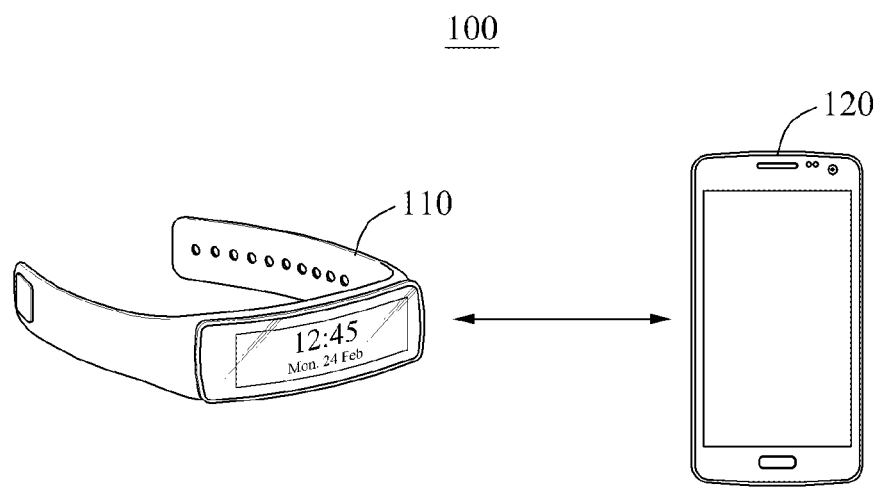
FIG. 1 is a diagram illustrating an example of a system to monitor a biosignal.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, examples will be described in detail with reference to the accompanying drawings.

The term "ward" indicates a person who is to be protected by a guardian or a caretaker. For example, the ward may include a person who has difficulty in freely expressing an opinion. Such a person may not readily inform another person of an emotion state and an occurrence of a predetermined accident. For example, a child may be taken into a daycare center or a kindergarten and a guardian, for example, a parent of the child may wonder how the child is getting along in the daycare center or the kindergarten.

A parent may install a closed-circuit television (CCTV) or an Internet protocol (IP) camera to monitor the daily life of a child spending time in a daycare center or being taken care of by a nanny at home. The parent may monitor a lifestyle of the child in real time or in a predetermined time zone. In this example, a nanny may be under stress since the nanny is also being continuously monitored. Due to the stress created by the real time monitoring, a person who takes care of a ward may not prefer a monitoring system.

FIG. 1 illustrates an example of a system 100 to monitor a biosignal (hereinafter, a biosignal monitoring system).

In an example, the biosignal monitoring system 100 recognizes an emotion event occurring from a lifestyle of a ward based on a biosignal of the ward, and informs a guardian of the emotion event. Hereinafter, the term "ward" used herein indicates a user. For example, the biosignal monitoring system 100 remotely informs a parent about an emotionally bad accident and state of a child experiencing when the child is committed to a daycare center or is being taken care by a nanny.

The term "emotion event" used herein indicates an event that defines an emotion. The term "emotion state" used herein indicates a current emotion state of the user. For example, the emotion state is classified based on whether the user is in a positive or negative emotion state, and an irritation level of the user. For example, the emotion state is classified into anger, tedium, joy, grief, and stress. However, it is only an example and thus, a variety of classification systems may be applied to classify the emotion state.

The term "biosignal" used herein indicates a signal measured from a body of the user and may include at least one of a bio-electrical signal, for example, an ExG signal, an electrocardiogram (ECG) signal, an electroencephalogram (EEG) signal, an electromyography (EMG) signal, and an electrooculogram (EOG) signal, a bio-optical signal, a skin temperature signal, a bio-impedance signal, and a pressure signal. For example, the biosignal may be a signal indicating a change in a volume of the chest caused by blood pressure and respiration.

The biosignal monitoring system 100 includes a device 110 to monitor a biosignal of a user (hereinafter, a biosignal monitoring device) and an external device 120.

The biosignal monitoring device 110 measures a biosignal from the user. The biosignal monitoring device 110 uses the measured biosignal to analyze an emotion event of the user.

The biosignal monitoring device 110 analyzes an emotion state of the user from the emotion event. Although the biosignal monitoring device 110 is illustrated as a wearable device in FIG. 1, it is only an example and any type of electronic device capable of measuring and analyzing a biosignal may be used for the biosignal monitoring device 110.

Furthermore, a change in an emotion state of a user may cause a change in a biosignal, for example, an acceleration in a heartbeat, an increase in a body temperature, and an increase in an amount of sweat on the skin. Accordingly, the emotion state of the user is estimated from a biosignal of the user. For example, the biosignal monitoring device 110 detects the change in the biosignal and compares a current biosignal against a biosignal in a state in which the user does not perceive any emotion, and analyzes the emotion event.

As described above, an emotion state of a child is estimated by measuring a biosignal of the child who is unaccustomed to expressing emotions and communications. A parent of the child verifies in which emotion state the child has spent a day, based on data acquired from biosignals monitored from the child, although the parent does not take care of the child directly. In addition, a person who takes care of the child does not incur the stress of being monitored and the parent who has left the child at a daycare center or with a nanny also verifies an emotion state that the child has perceived during a day.

Also, the biosignal monitoring device 110 controls the external device 120 in response to the emotion event analyzed from the biosignal of the user. Here, the external device 120 includes a device to perform an additional function in response to the emotion state of the user. For example, when the external device 120 is a device that plays back music, the external device 120 is controlled to adjust a volume or select a predetermined song based on the emotion state of the user. Also, when the external device 120 is a lighting device, the external device 120 is controlled to adjust the intensity of irradiation based on the emotion state of the user.

Although the external device 120 is illustrated as a smartphone in FIG. 1, it is only an example and thus, any type of electronic devices capable of performing an additional function may be used for the external device 120.

Hereinafter, the additional function used herein may indicate a function for affecting an emotion of the user in response to an emotion state of the user and the additional function may be performed by the biosignal monitoring device 110, the external device 120, and a device 710 of FIG. 7 to analyze a biosignal (hereinafter, a biosignal analyzing device). For example, when the user is in a negative emotion state, the additional function includes an operation of adjusting a volume or selecting a song so that the user may be in a positive emotion state. As another example, when the user is in an irritated state, the additional function includes an operation of decreasing the intensity of irradiation so that the user may be in a stable state.

Figure 2:
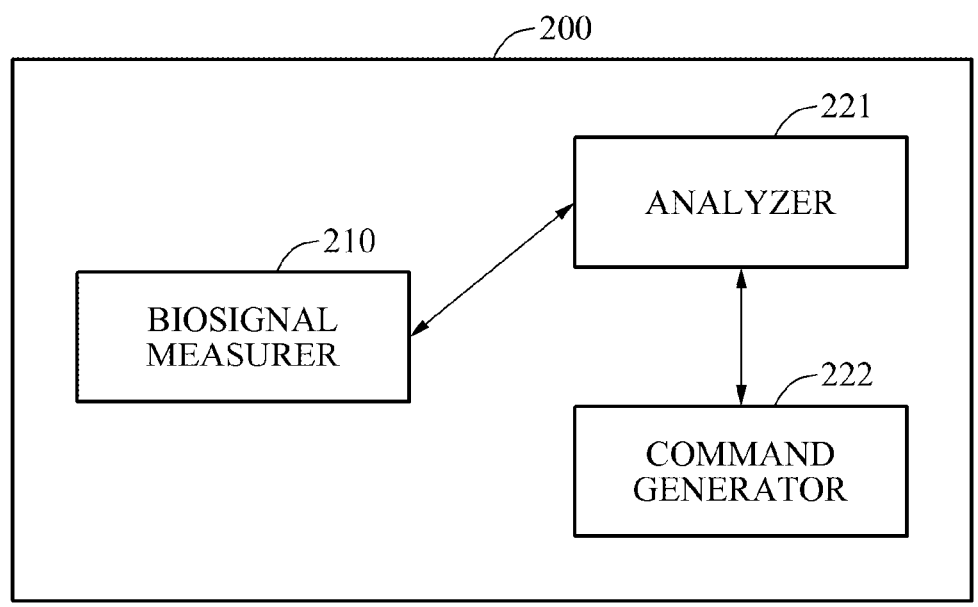
FIGS. 2 and 3 are block diagrams illustrating examples of a device to monitor a biosignal of a user.
Figure 3:
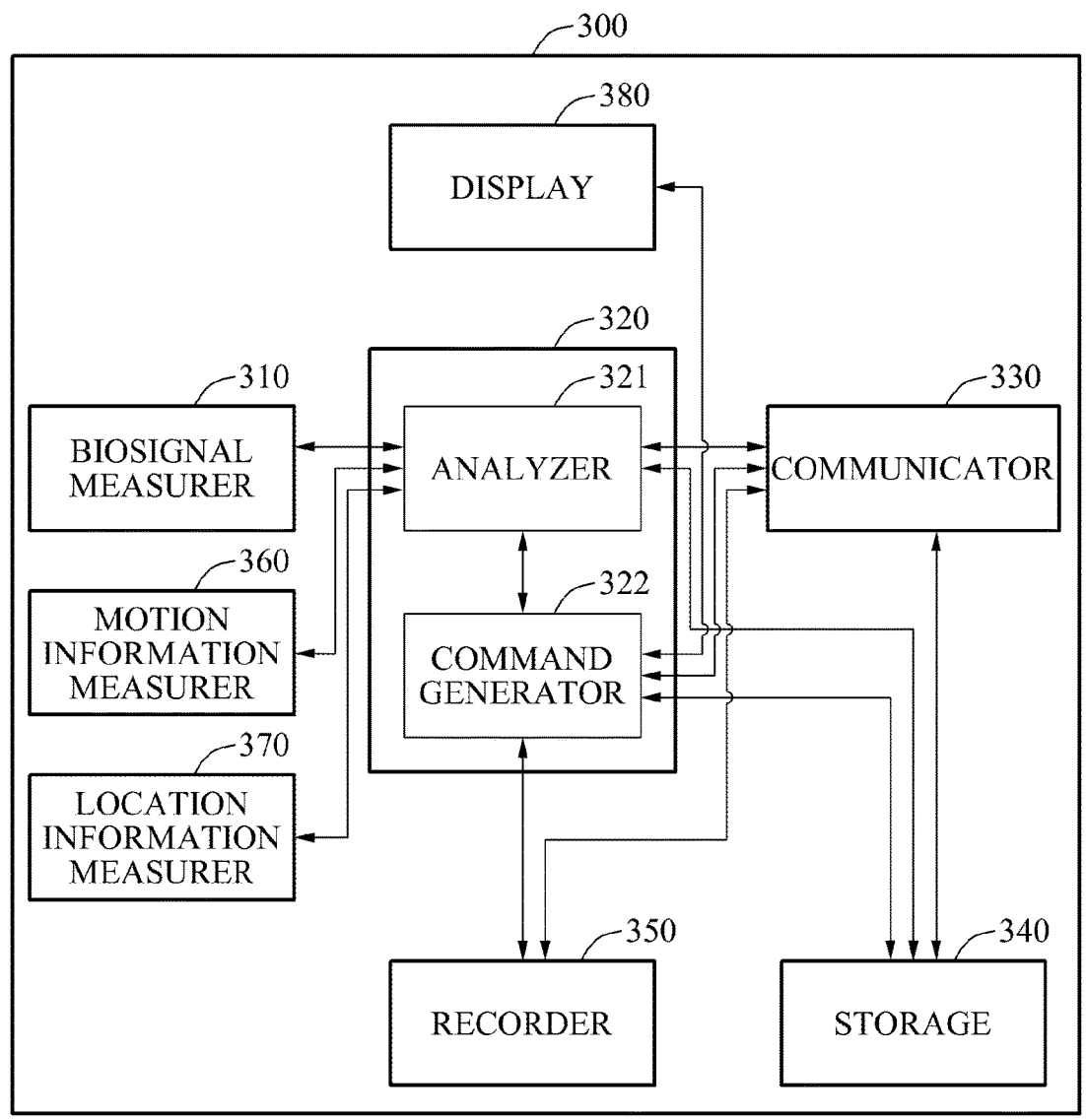

FIGS. 2 and 3 illustrate examples of a biosignal monitoring device 200.

FIG. 2 illustrates an example of a configuration of the biosignal monitoring device 200.

Referring to FIG. 2, the biosignal monitoring device 200 includes a biosignal measurer 210, an analyzer 221, and a command generator 222.

The biosignal measurer 210 measures a biosignal from a user. Here, the biosignal refers to a signal associated with a body of the user and may include a bio-electrical signal, for example, an ExG signal, an ECG signal, an EEG signal, an EMG signal, and an EOG signal, a bio-optical signal, a skin temperature signal, a bio-impedance signal, and a pressure signal, for example, a signal indicating a change in a volume of the chest caused by blood pressure and respiration. For example, the biosignal measurer 210 measures a biosignal through indirect contact with the body of the user, which will be further described with reference to FIGS. 4 and 10.

The analyzer 221 analyzes an emotion event associated with the user based on the biosignal. Here, the analyzer 221 detects a change corresponding to a predetermined range or a predetermined pattern from the biosignal. The emotion event associated with the user may include an event that the biosignal indicates a change in the predetermined range or an event that the biosignal indicates a change in a predetermined pattern.

For example, the analyzer 221 recognizes, as "irritation or anger", a state in which a current blood pressure or body temperature currently detected by the biosignal measurer 210 is greater by at least a predetermined level than a reference value. The reference value may be for example, a value measured in a state in which the user does not perceive any emotion, or an average value, for example, an average in a predetermined time interval during monitoring. They analyzer 221 further recognizes, as "tension", a state in which current skin resistance measured by the biosignal measurer 210 is less by a predetermined level than the reference value or the average value. When the user is tense, the user produces sweat more than usual and when more sweat is produced, the skin resistance decreases. A body state and an emotion state recognized as above may be variously added or modified through an experiment. Also, more reliable cognitive data may be acquired through a combination of recognized states.

Also, the analyzer 221 recognizes an emotion state of the user as "tedium" based on biosignals associated with a skin temperature, a skin resistance level, a frequency of ECG and ECG of respiration. The analyzer 221 recognizes an emotion state of the user as "anger" based on biosignals associated with the skin resistance level and ECG of respiration. The analyzer 221 recognizes an emotion state of the user as "joy" based on biosignals associated with the number of heartbeats, a frequency of ECG, and a respiration rate. The analyzer 221 recognizes an emotion state of the user as "grief" based on biosignals associated with the number of heartbeats and the skin resistance level. The analyzer 221 recognizes an emotion state of the user as "stress" based on biosignals associated with the skin resistance level.

The command generator 222 generates a control command in response to a result of analyzing the emotion event. The result of analyzing the emotion event may include a time and a location at which the emotion event has occurred, and an emotion state of the user. The control command refers to a command for controlling at least one of the biosignal monitoring device 200 and an external device, and is generated as digital data or analog data.

For example, the command generator 222 generates a control command for controlling the external device to perform a predetermined operation in response to the result of analyzing the emotion event. When the external device is a device that plays back music, the control command includes a command for adjusting a volume or selecting a predetermined song based on the emotion state of the user. When the external device is a lighting device, the control command includes a command for adjusting the intensity of irradiation based on the emotion state of the user.

The command generator 222 generates a control command corresponding to the emotion state in response to the emotion state of the user analyzed from the emotion event. For example, the command generator 222 generates a control command for controlling the biosignal monitoring device 200 and the external device to perform an operation that induces the user to be in a positive emotion state when the user is in a negative emotion state. Also, the control command includes a command for controlling the biosignal monitoring device 200 and the external device to perform an operation that leads to a positive emotion of the user and to maintain the positive emotion state of the user.

For example, when the emotion state of the user is an anger state, the command generator 222 generates a control command for decreasing the intensity of irradiation of a lighting or a volume of music.

FIG. 3 illustrates an example of a configuration of a biosignal monitoring device 300.

Referring to FIG. 3, the biosignal monitoring device 300 includes a biosignal measurer 310, an analyzer 321, a command generator 322, a communicator 330, a storage 340, a recorder 350, a motion information measurer 360, a location information measurer 370, and a display 380. The biosignal measurer 310, the analyzer 321, and the command generator 322 may be configured to be similar to the biosignal measurer 210, the analyzer 221, and the command generator 222 of FIG. 2.

A micro control unit (MCU) 320 includes the analyzer 321 and the command generator 322, but is not limited thereto. For example, a biosignal measured by the biosignal measurer 310 is transferred to the MCU 320 and is analyzed by the MCU 320. As another example, a biosignal is transferred to an external device configured to analyze a biosignal through the communicator 330 and is analyzed by the external device.

The communicator 330 transmits event information associated with the emotion event to the external device. For example, the communicator 330 is connected to the external device through wired or wireless communication. Here, the wired communication includes an interface, for example, a universal serial bus (USB) for transferring data, but is not limited thereto. For example, the external device includes a manager terminal used by a guardian and the like to receive the event information. Event information associated with the emotion event may include image information, sound information, emotion information, and bio-information corresponding to an emotion event.

Image information corresponding to an emotion event may include an image of a user of which the emotion event has occurred and an image around the user. Sound information corresponding to the emotion event may include a sound of the user of which the emotion event has occurred and a sound around the user. Emotion information corresponding to the emotion event may include an emotion state of the user when the emotion event occurred. Bio-information corresponding to the emotion event may include a biosignal of the user when the emotion event occurred.

When the emotion event is determined to be a predetermined emotion state, the command generator 322 generates a control command for controlling the communicator 330 to transmit event information to the external device. For example, when the emotion event is analyzed as a negative emotion state, the command generator 322 transmits event information to the external device.

The storage 340 generates and stores event information in response to a result of analyzing the emotion event. For example, in response to an occurrence of an emotion event, the storage 340 generates and stores event information corresponding to the emotion event. Also, the storage 340 may store a biosignal in real time.

The command generator 322 generates a control command for controlling the communicator 330 to provide event information to the external device in response to a connection request of the external device to the event information. For example, the command generator 322 provides event information to the external device in response to an authenticated connection request, that is, when the connection request is authenticated.

For example, instead of transmitting event information every time an emotion event occurs, the biosignal monitoring device 300 repeats a storing operation and transmits event information when a connection request is received. Accordingly, it is possible to minimize an amount of power consumed and to maximize a use time of the biosignal monitoring device 300. The biosignal monitoring device 300 may be configured to store a biosignal and an emotion state of the user in a simplest manner by not including the recorder 350 or by excluding a wireless communication function from the communicator 330. Accordingly, a size of a portable device may be minimized.

The recorder 350 records at least one of image information and sound information associated with the user and an ambient environment of the user. The recorded image information and sound information is stored in the storage 340 as event information. When the emotion event is determined to be a predetermined emotion state, the communicator 330 transmits at least one of image information and sound information corresponding to a time interval in which the emotion event has occurred. For example, the predetermined emotion state may include a negative emotion state, a positive emotion state, an irritated emotion state, and a stable emotion state. In this example, a guardian holding the external device may receive an image and a sound associated with the user and an ambient environment of the user when the user, for example, a ward perceives a negative or a positive emotion.

The motion information measurer 360 measures motion information of the user. Here, the motion information refers to information associated with a motion of the user, and may include an acceleration of the user, for example, an acceleration about three axes or acceleration about six axes, a magnetic field of an earth axis affecting the user, and an equilibrium state of the user. The analyzer 321 determines an emotion event based on a change in a biosignal associated with the motion information. For example, the analyzer 321 may more accurately analyze an emotion event by excluding a change in a biosignal associated with a motion of the user and by analyzing the biosignal.

The location information measurer 370 measures location information of the user. For example, the location information measurer 370 may measure location information of the user through a global positioning system (GPS). Here, the analyzer 321 determines an emotion event based on location information. For example, the analyzer 321 may further accurately analyze an emotion event by excluding a change in a biosignal unassociated with an emotion of the user from location information and by analyzing the biosignal. For example, when the user is located on a playground, the user is highly likely to be playing and thus, the analyzer 321 may exclude a change in a biosignal caused by exercise and may analyze the biosignal.

The display 380 displays event information. For example, the display 380 may display bio-information and emotion information of the user.

Figure 4:
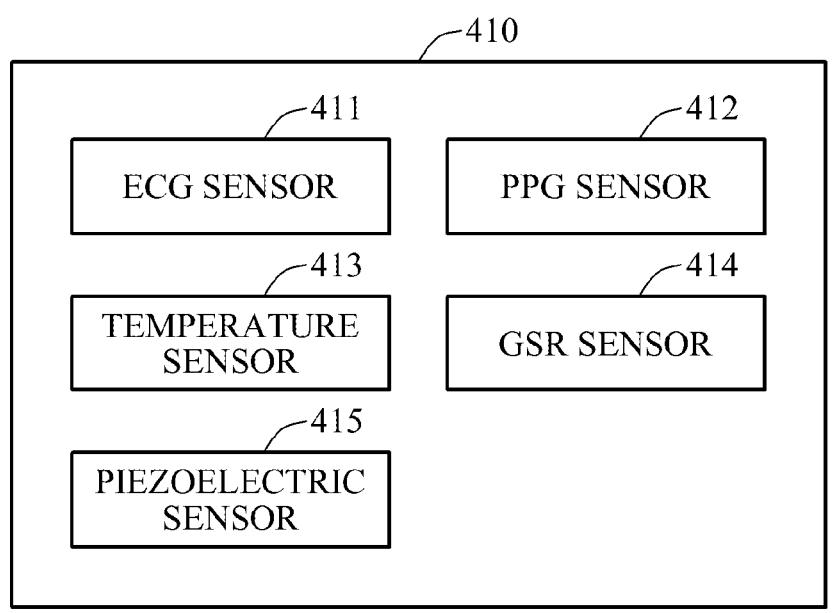
FIG. 4 is a block diagram illustrating an example of a biosignal measurer.

FIG. 4 illustrates an example of a biosignal measurer.

The biosignal measurer 410 refers to a sensor configured to measure a biosignal from a user, and includes sensors. Referring to FIG. 4, the biosignal measurer 410 includes an ECG sensor 411, a photoplethymogram (PPG) sensor 412, a temperature sensor 413, a galvanic skin response (GSR)

sensor 414, and a piezoelectric sensor 415. The ECG sensor 411 senses an ECG signal that is an electrical signal occurring at the heart, the PPG sensor 412 senses a PPG signal that is an optical signal varying due to the blood flow, the temperature sensor 413 senses a temperature of the skin surface, the GSR sensor 414 senses a GSR signal that is an impedance of the skin surface, and the piezoelectric sensor 415 senses a piezoelectric signal that is a change in the pressure of the sensor surface attached onto the skin.

Figure 5:
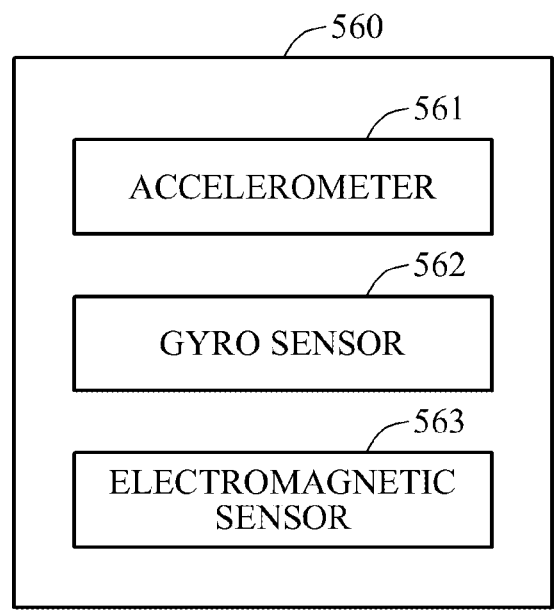
FIG. 5 is a block diagram illustrating an example of a motion information measurer.

FIG. 5 illustrates an example of a motion information measurer.

The motion information measurer 560 refers to a sensor configured to measure a motion of a user and includes sensors. Referring to FIG. 5, the motion information measurer 560 includes an accelerometer 561, a gyro sensor 562, and an electromagnetic sensor 563. The accelerometer 561 senses an acceleration of the user, the gyro sensor 562 senses an equilibrium state of the user, and the electromagnetic sensor 563 senses a magnetic field of an earth axis affecting the user.

The aforementioned motion information is used when the analyzer 321 of FIG. 3 excludes a change in a biosignal caused by a factor excluding an emotion.

Figure 6:
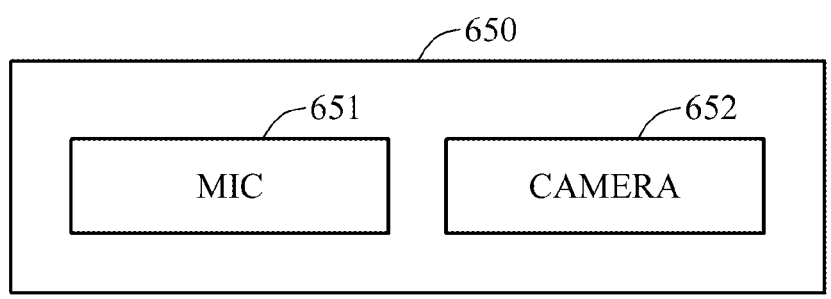
FIG. 6 is a block diagram illustrating an example of a recorder.

FIG. 6 illustrates an example of a recorder.

The recorder 650 includes a microphone (MIC) 651 and a camera 652. The microphone 651 records a sound of a user and a sound around the user. The camera 652 records an image of the user and an image around the user. Here, the recorder 650 is embedded within a biosignal monitoring device or may also be configure as an independent external device.

Figure 7:
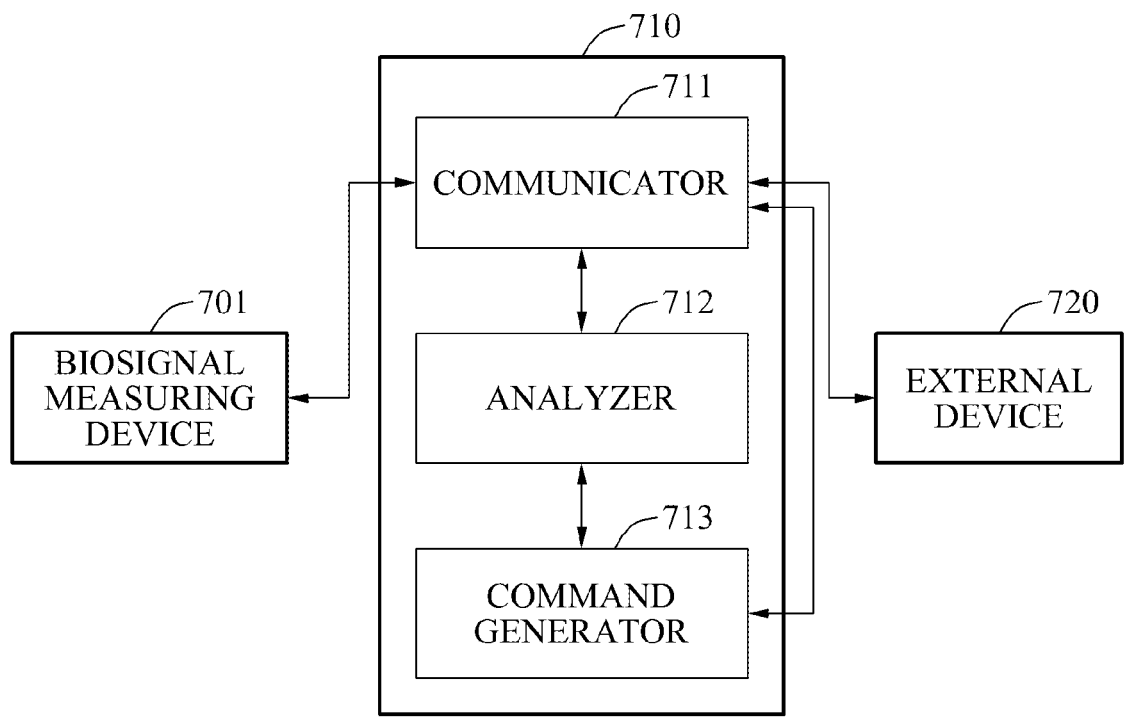
FIG. 7 is a block diagram illustrating an example of a system to analyze a biosignal.

FIG. 7 illustrates an example of a system to analyze a biosignal.

Referring to FIG. 7, the system 700 (hereinafter biosignal analyzing system 700) includes a biosignal measuring device 701, a biosignal analyzing device 710, and an external device 720.

The biosignal measuring device 701 refers to a device configured to measure a biosignal of a user, and configured to transmit the measured biosignal to the biosignal analyzing device 710. For example, the biosignal measuring device 701 may process and transmit a biosignal. Here, processing the biosignal may include removing noise in the biosignal and compressing the biosignal in which the noise is removed.

The biosignal analyzing device 710 includes a communicator 711, an analyzer 712, and a command generator 713.

The communicator 711 receives, from the biosignal measuring device 701, the biosignal measured from the user. For example, the communicator 711 may receive a biosignal through wired or wireless communication.

The analyzer 712 analyzes an emotion event associated with the user based on the biosignal.

The command generator 713 generates a control command for controlling at least one of the biosignal analyzing device 710 and the external device 720 in response to the emotion event. For example, the command generator 713 may generate a control command to perform an operation corresponding to an emotion state of the user in response to an analysis of the emotion event.

For example, when the biosignal analyzing device 710 provides an additional function, the command generator 713 may generate a control command for controlling the biosignal analyzing device 710 to perform an additional function corresponding to a predetermined emotion state. As another example, when the external device 720 provides an additional function, the command generator 713 may generate a control command for controlling the external device 720 to perform an additional function corresponding to a predetermined emotion state.

Figure 8:
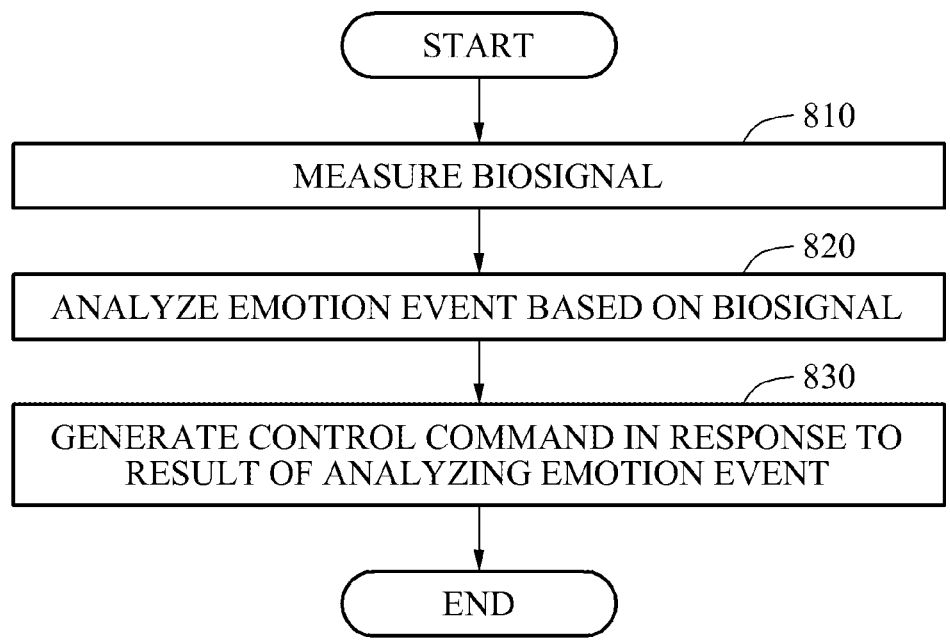
FIG. 8 is a flowchart illustrating an example of a method to monitor a biosignal.

FIG. 8 illustrates an example of a method of monitoring a biosignal.

In operation 810, a biosignal measurer measures a biosignal. Biosignals sensed at sensors are transmitted to an MCU and used to determine an emotion state of a user.

In operation 820, an analyzer analyzes an emotion event based on the biosignal. Event information including a result of analyzing the biosignal and the measured biosignal are stored in a storage. Here, the analyzer may determine an emotion event based on a change in a biosignal associated with motion information and location information of the user.

In operation 830, a command generator generates a control command in response to the result of analyzing the emotion event. The command generator may generate a control command for controlling an external device to perform a predetermined operation in response to the result of analyzing the emotion event. The predetermined operation may indicate an operation of performing an additional function.

In an example, the command generator may generate a control command for activating at least one of additional functions when the analyzed emotion event is determined to be a negative emotion state. For example, the additional function may include an alarm function, for example, a function of alerting a guardian of an emotion state of a ward, using a wireless communication function and a function of recording and transmitting a video and a sound of a user or around the user. Also, the additional function may include a function of transmitting event information associated with the emotion event through a connection to an external device of a third party, for example, a guardian using a wireless communication function.

Figure 9:
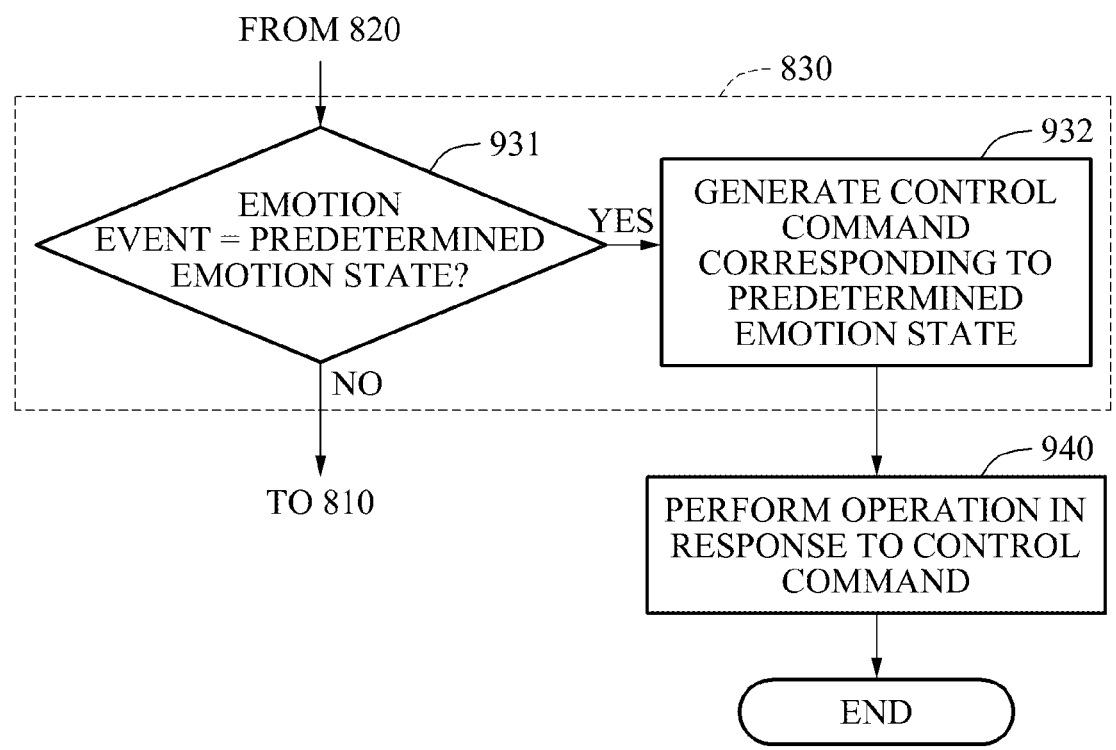
FIG. 9 is a flowchart illustrating an example of a method to generate a control command in response to a result of analyzing an emotion event.

FIG. 9 illustrates an example of a method to generate a control command in response to a result of analyzing an emotion event.

Operation 830 of FIG. 8 are performed as follows.

In operation 931, an analyzer determines whether the emotion event is a predetermined emotion state. For example, the analyzer may determine whether the emotion state of the user is the predetermined emotion state, for example, a positive state, a negative state, an irritated state, and a stable state, based on a biosignal of the user. Here, in terms of the emotion state of the user, each of a positive level, a negative level, an irritated level, and a stable level is classified into a plurality of levels.

In operation 932, the command generator generates a control command corresponding to the predetermined emotion state. For example, when the emotion event is determined to be a predetermined emotion state, the command generator may generate a control command for transmitting event information. When the emotion event is determined to be the predetermined emotion state, the command generator may generate a control command for generating and storing event information. When the emotion event is determined to be the predetermined emotion state, the command generator may generate a control command for transmitting at least one of image information and sound information corresponding to a time interval in which the emotion event has occurred.

In operation 940, an external device, a biosignal monitoring device, and a biosignal analyzing device perform an operation in response to the control command. For example, at least one of the external device, the biosignal monitoring device, and the biosignal analyzing device may perform an operation in response to each control operation described in operation 932. Here, examples of the control command are not limited thereto and may include any type of control commands generated in response to the emotion state of the user.

Figure 10:
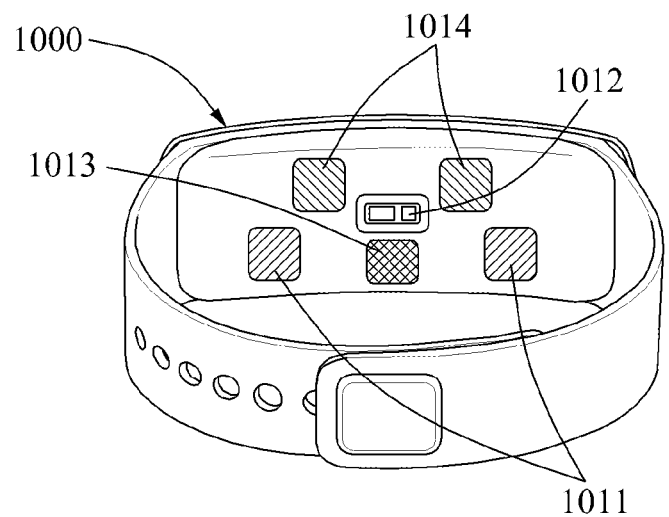
FIG. 10 is a diagram illustrating an example of a device to monitor a biosignal of a user.

FIG. 10 is a diagram illustrating an example of a device to monitor a biosignal of a user.

For example, the device 1000 (hereinafter, a biosignal monitoring device) is configured as a wearable device. The biosignal monitoring device 1000 of FIG. 10 is provided in form of a watch wearable around a wrist, and includes a variety of sensors configured to measure a biosignal. The sensors are attached on a lower side, for example, a skin contact surface of the biosignal monitoring device 1000. For example, the variety of sensors may include an ECG sensor 1011, a PPG sensor 1012, a temperature sensor 1013, and a GSR sensor 1014.

The biosignal monitoring device 1000 is separated into a body and a strap. Electrodes for measuring a biosignal or skin contact portions are positioned on the body or the strap. The strap is made of rubber, plastic, a conductive fiber, and a general fiber, but is not limited thereto and any other suitable material may be used to make the strap.

The units, measurer, analyzer and generator described herein may be implemented using hardware components. For example, the hardware components may include controllers, microphones, amplifiers, band-pass filters, audio to digital convertors, and processing devices, but are not limited thereto. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such as parallel processors.

The methods according to embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as floptical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly other implementations are within the scope of the following claims.

What is claimed is:

1. A device configured to monitor a biosignal of a user of the device, the device comprising:
   a biosignal measurer configured to measure a biosignal from the user;
   an analyzer configured to analyze an emotion event associated with the user based on the biosignal to produce a result comprising an emotion state of the user and a time and a location at which the emotion state occurs;
   a command generator configured to generate a control command in response to the result; and
   a communicator configured to transmit at least one of image information and sound information associated with the user and corresponding to a time interval in which the emotion event has occurred, in response to the emotion event being determined to be a predetermined emotion state.

2. The device of claim 1, wherein the control command generated by the command generator controls an external device to perform a predetermined operation in response to the result of analyzing the emotion event.

3. The device of claim 1, wherein the control command generated by the command generator corresponds to the emotion state of the user.

4. The device of claim 1, wherein:
   the communicator is further configured to transmit event information associated with the emotion event to an external device, the event information comprising either one or both of image information of the user and a surrounding area of the user during the emotion event or sound information of the user and the surrounding area of the user during the emotion event.

5. The device of claim 4, wherein the control command generated by the command generator controls the communicator to transmit the event information in response to the emotion event being determined to be the predetermined emotion state.

6. The device of claim 4, further comprising:
   a storage configured to generate and store the event information in response to the result of analyzing the emotion event,
   wherein the control command generated by the command generator controls the communicator to provide the event information to the external device in response to a connection request of the external device to the event information.

7. The device of claim 1, further comprising:
   a recorder configured to record at least one of image information and sound information associated with at least one of the user and an ambient environment of the user.

8. The device of claim 1, further comprising:
   a motion information measurer configured to measure motion information of the user of the device,
   wherein the analyzer is configured to determine the emotion event based on a change in a biosignal associated with the motion information.

9. The device of claim 1, further comprising:
a location information measurer configured to measure location information of the user of the device,
wherein the analyzer is configured to determine the emotion event based on the location information.

10. The device of claim 1, wherein the biosignal comprises at least one of a bio-electrical signal, a bio-optical signal, a skin temperature signal, a bio-impedance signal, and a pressure signal.

11. A device configured to analyze a biosignal of a user of the device, the device comprising:
a communicator configured to receive a biosignal measured from the user of the device;
an analyzer configured to analyze an emotion event associated with the user of the device based on the biosignal to produce a result comprising an emotion state of the user and a time and a location at which the emotion state occurs; and
a command generator configured to generate a control command for controlling at least one of the device or an external device in response to the result,
wherein the communicator is further configured to transmit at least one of image information and sound information associated with the user and corresponding to a time interval in which the emotion event has occurred, in response to the emotion event being determined to be a predetermined emotion state.

12. The device of claim 11, wherein the control command generated by the command generator controls at least one of the device or the external device to perform an operation corresponding to the emotion state of the user of the device.

13. A method to monitor a biosignal of an individual, the method comprising:
measuring a biosignal from the individual;
analyzing an emotion event associated with the individual based on the biosignal to produce a result comprising an emotion state of the individual and a time and a location at which the emotion state occurs;
generating a control command in response to the result of analyzing the emotion event; and
transmitting at least one of image information and sound information associated with the user and corresponding to a time interval in which the emotion event has occurred, in response to the emotion event being determined to be a predetermined emotion state.

14. The method of claim 13, wherein the generated control command controls an external device to perform a predetermined operation in response to the result of analyzing the emotion event.

15. The method of claim 13, wherein the generated control command corresponds to the emotion state of the individual.

16. The method of claim 13, further comprising:
transmitting event information associated with the emotion event to an external device, the event information comprising either one or both of image information of the individual and a surrounding area of the individual during the emotion event or sound information of the individual and the surrounding area of the individual during the emotion event.

17. The method of claim 16, further comprising:
generating and storing the event information in response to the result of analyzing the emotion event,
wherein the transmitting of the event information comprises providing the event information to the external device in response to a connection request of the external device to the event information.

18. The method of claim 13, further comprising:
recording at least one of image information and sound information associated with at least one of the individual and an ambient environment of the individual.

19. The method of claim 13, further comprising:
measuring at least one of motion information and location information of the individual,
wherein the analyzing of the emotion event comprises determining the emotion event based on a change in a biosignal associated with at least one of the motion information and the location information.

* * * * *